United States Patent
Pyun et al.

(10) Patent No.: US 10,492,690 B2
(45) Date of Patent: Dec. 3, 2019

(54) TIP FOR LASER HANDPIECE

(71) Applicant: Speclipse, Inc., Seoul (KR)

(72) Inventors: Sung Hyun Pyun, Seoul (KR); Wanki Min, Gyeonggi-do (KR)

(73) Assignee: SPECLIPSE, INC., Seoul (KR)

( * ) Notice: Subject to any disclaimer, the term of this patent is extended or adjusted under 35 U.S.C. 154(b) by 255 days.

(21) Appl. No.: 15/810,803

(22) Filed: Nov. 13, 2017

(65) Prior Publication Data
US 2019/0029520 A1 Jan. 31, 2019

(30) Foreign Application Priority Data

Jul. 28, 2017 (KR) .......................... 10-2017-0095877
Sep. 18, 2017 (KR) .......................... 10-2017-0119631

(51) Int. Cl.
| | | |
|---|---|---|
| G02B 9/00 | (2006.01) | |
| A61B 5/00 | (2006.01) | |
| G02B 27/09 | (2006.01) | |
| G02B 27/40 | (2006.01) | |
| G01J 3/02 | (2006.01) | |

(52) U.S. Cl.
CPC .......... *A61B 5/0075* (2013.01); *A61B 5/0059* (2013.01); *A61B 5/0077* (2013.01); *A61B 5/441* (2013.01); *G01J 3/021* (2013.01); *G01J 3/0208* (2013.01); *G01J 3/0218* (2013.01); *G01J 3/0291* (2013.01); *G02B 27/0988* (2013.01); *G02B 27/0994* (2013.01); *G02B 27/40* (2013.01); *A61B 2562/0233* (2013.01)

(58) Field of Classification Search
CPC .................................................. A61B 5/0075
USPC ......................................................... 359/738
See application file for complete search history.

(56) References Cited

U.S. PATENT DOCUMENTS

| | | | |
|---|---|---|---|
| 9,377,395 B2 | 6/2016 | Aharon | |
| 9,709,529 B2 * | 7/2017 | Takats | .................... G01N 1/286 |
| 9,907,472 B2 | 3/2018 | Pyun et al. | |

(Continued)

FOREIGN PATENT DOCUMENTS

| | | | | |
|---|---|---|---|---|
| JP | 4749805 | | 5/2011 | ............. G01N 21/65 |
| KR | 10-1998-0067406 A | | 10/1998 | |

(Continued)

OTHER PUBLICATIONS

International Search Report (ISR) from corresponding PCT Application No. PCT/KR2018/008080, dated Oct. 19, 2018.

(Continued)

*Primary Examiner* — James C. Jones
(74) *Attorney, Agent, or Firm* — Harness, Dickey & Pierce, P.L.C.

(57) ABSTRACT

According to one embodiment, a tip for a laser handpiece includes: a light radiating module configured to radiate a laser toward a target; and a light receiving module configured to receive at least a portion of light which is generated by the laser radiated onto the target as received light. The light radiating module includes: a base which has an inner space formed therein to allow the laser to pass therethrough; a fixing portion which is coupled to a lower portion of the base and has a penetrating hole formed therein to allow the laser to pass therethrough; and a module connecting member which is interposed and fixed between the base and the fixing portion.

21 Claims, 13 Drawing Sheets

(56) References Cited

U.S. PATENT DOCUMENTS

2008/0007716 A1    1/2008   Igarashi
2018/0304093 A1   10/2018   Son

FOREIGN PATENT DOCUMENTS

| KR | 10-2013-0123426 | 11/2013 | ............ G01N 21/21 |
| KR | 10-1587771 B1 | 1/2016 | |
| KR | 10-1640202 | 7/2016 | ............... A61B 5/00 |
| KR | 10-1647022 B1 | 8/2016 | |
| KR | 10-2017-0073223 A | 6/2017 | |
| KR | 10-2017-0073298 A | 6/2017 | |

OTHER PUBLICATIONS

International Search Report (ISR) from corresponding PCT Application No. PCT/KR2018/008134, dated Oct. 19, 2018.
Office Action from corresponding Korean Patent Application No. 10-2017-0095877, dated Jan. 16, 2019.
Office Action from corresponding Korean Patent Application No. 10-2017-0119631, dated Dec. 13, 2018.

* cited by examiner

TIP FOR LASER HANDPIECE

CROSS REFERENCE TO RELATED APPLICATIONS

The present application claims priority to Korean Patent Application Nos. 10-2017-0095877 filed on Jul. 28, 2017 and 10-2017-0119631 filed Sep. 18, 2017 in the Republic of Korea, the disclosures of which are incorporated herein by reference

FIELD

The present invention relates to a tip for a laser handpiece which is mountable in a handpiece of a laser device, and more particularly, to a tip for a laser handpiece for diagnosis which can adjust laser energy to be radiated onto a target.

BACKGROUND

In recent years, laser technology (refer to patent document 1) for diagnosing diseases by radiating lasers onto a skin using a related-art laser device for skin treatment and beauty, and analyzing a spectrum of light generated by the radiated lasers is developing.

FIG. 1 schematically illustrates a related-art laser device for skin treatment and beauty care which is utilized to diagnose diseases. Referring to FIG. 1, a laser L1 is generated at a laser generator 2 and is transmitted to a handpiece 1 through an optical fiber or the like, and then is radiated onto a target T (for example, a patient's skin) and a portion of light generated at the target T is collected at a light receiver 3 as received light L2. A spectrometer 4 extracts a spectrum of the light received at the light receiver 3, and a data processing unit 5 analyzes spectrum data and performs a necessary task such as diagnosing a disease or measuring a skin age. The result is provided to a user through a display 6.

However, in such a related-art laser device, a light radiating unit (for example, the handpiece 1) for radiating the laser L1 onto the target, and the light receiver 3 for receiving (collecting) the received light L2 are separately installed. Therefore, there are disadvantages that many components are required and the device has a complicated configuration, and a volume increase.

In addition, the related-art laser device for skin treatment and beauty care as described above (for example, Nd:YAG, Ruby, Alexandrite laser device, or the like) may radiate lasers of relatively high energy for the purpose of removing a pigment from skin or treating a skin through destruction and recovery of tissue (for example, about 100-1600 mJ per pulse). Accordingly, there may be thermal damage to a skin when the related-art laser device for skin treatment and beauty care is directly utilized for disease diagnosis.

[Patent Documents]
Patent Document 1: Korean Patent Registration No. 10-1640202 (Jul. 21, 2016)
Patent Document 2: Korean Patent Publication No. 10-2013-0123426 (Nov. 12, 2013)
Patent Document 3: Japanese Patent Registration No. 4749805 (May 27, 2011)

SUMMARY

Technical Objects
According to one embodiment of the present invention, there is provided a tip for a laser handpiece for diagnosis, which can diagnose diseases or measure a skin age using a related-art laser device as it is.

According to another embodiment of the present invention, there is provided a tip for a laser handpiece for diagnosis, which is easily mountable in or dismountable from a handpiece of a related-art laser device for beauty care, and has a light radiating unit and a light receiving unit integrated thereinto.

Technical Solving Means
According to one embodiment of the present invention, there is provided a laser handpiece, including: a light radiating module configured to radiate a laser toward a target; and a light receiving module configured to receive at least a portion of light which is generated by the laser radiated onto the target as received light, wherein the light radiating module includes: a base which has an inner space formed therein to allow the laser to pass therethrough; a fixing portion which is coupled to a lower portion of the base and has a penetrating hole formed therein to allow the laser to pass therethrough; and a module connecting member which is interposed and fixed between the base and the fixing portion, and wherein the light receiving module is coupled to the module connecting member, such that the light radiating module and the light receiving module are integrally coupled to a laser handpiece.

According to another embodiment of the present invention, there is provided a tip for a laser handpiece, including: a light radiating module configured to radiate a laser toward a target; and a light receiving module configured to receive at least a portion of light which is generated by the laser radiated onto the target as received light, wherein the light radiating module includes a base which has a first inner space to allow the laser to pass therethrough and a second inner space to allow the received light to pass therethrough, wherein the light receiving module is coupled to the base of the light radiating module such that the light radiating module and the light receiving module are integrally coupled to a laser handpiece.

Advantageous Effect
According to one or more embodiments of the present invention, there is an advantage that a disease is diagnosed or a skin age is measured by using a related-art laser device for beauty care as it is.

According to one or more embodiments of the present invention, a tip for a laser handpiece which has a light radiating unit and a light receiving unit integrated thereinto is provided, such that a laser device can be simplified and a volume thereof can be reduced compared to a related-art device in which a light radiating unit and a light receiving unit are separately installed.

According to one or more embodiments of the present invention, a tip for a laser handpiece which has a light radiating unit and a light receiving unit integrated thereinto is implemented, such that generated light can be received simply by attaching the tip to handpiece without requiring a separate light receiving device, and data processing for disease diagnosis can be performed based on the received light.

According to one or more embodiments of the present invention, an energy spectrum of a related-art laser device for skin treatment and beauty care is not required to be separately changed, and, simply by replacing the tip for the handpiece according to the present invention, lasers used for skin treatment and beauty care may be directly utilized for the purpose of disease diagnosis.

According to one or more embodiments of the present invention, an energy spectrum of a related-art laser device for skin treatment and beauty care is not required to be separately changed, and a spectrum signal for achieving the purpose of disease diagnosis can be detected without causing thermal damage to a skin.

DETAILED DESCRIPTION

Figure 1:
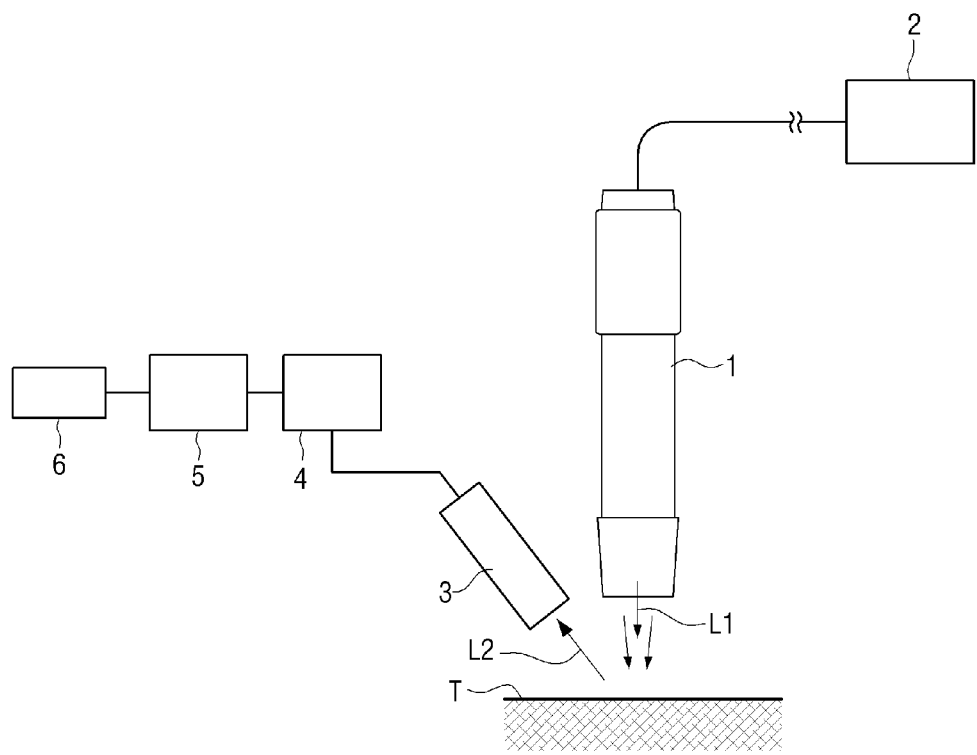
FIG. 1 is a view to illustrate a related-art laser device.

Exemplary embodiments will now be described more fully with reference to the accompanying drawings to clarify aspects, other aspects, features and advantages of the present invention. The exemplary embodiments may, however, be embodied in many different forms and should not be construed as limited to the exemplary embodiments set forth herein. Rather, the exemplary embodiments are provided so that this disclosure will be thorough and complete, and will fully convey the scope of the application to those of ordinary skill in the art.

In the drawings, length, thickness, width or the like of elements may be exaggerated and represented for effective explanation of the technical features.

As used herein, the singular forms are intended to include the plural forms as well, unless the context clearly indicates otherwise. It will be understood that the terms "comprises" and/or "comprising," when used in this specification, do not preclude the presence or addition of one or more other components.

It will be understood that when an element is referred to as being "on" another element, the element can be directly on another element or intervening elements. The terms "unit" and "module" and the terms having suffix "-er" or "-or" used in the description of this application refer to a unit for processing at least one function or operation, and may be implemented by hardware, software, or a combination of hardware and software.

Hereinafter, the present invention will be described in greater detail with reference to the accompanying drawings. In describing specific embodiments, various specific features are described to assist in a detailed description and a comprehensive understanding of the present invention. However, it is apparent that the exemplary embodiments can be carried out by those of ordinary skill in the art without those specifically defined features. In the description of exemplary embodiments, certain detailed explanations of portions which are well known and have nothing to do with the present invention are omitted when it is deemed that they may unnecessarily obscure the essence of the present invention.

Figure 2:
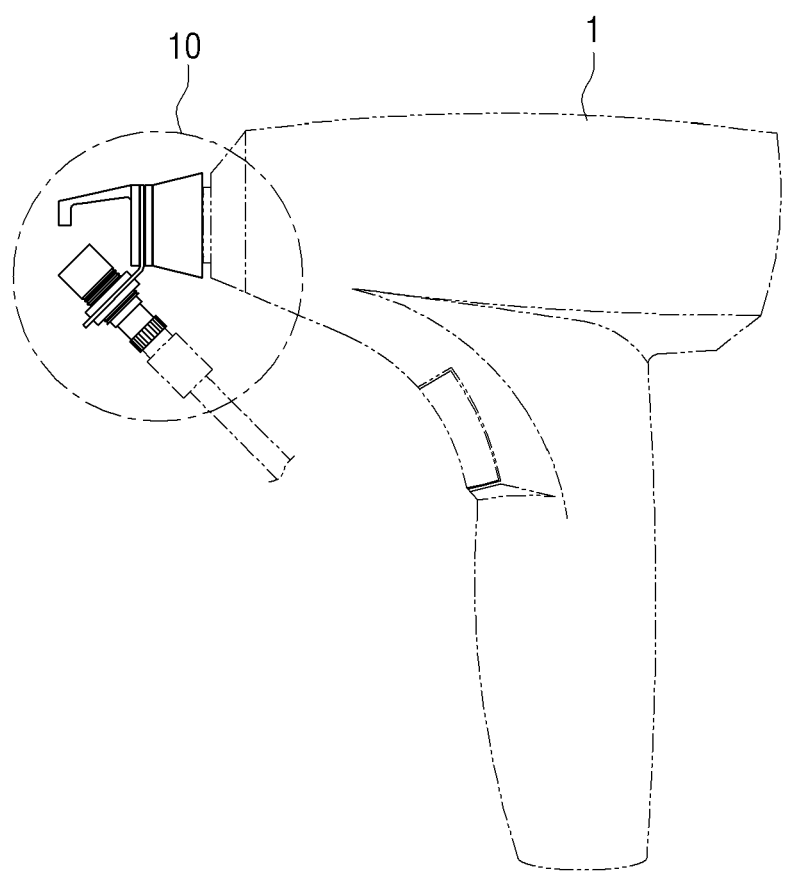
FIG. 2 is a view to illustrate a tip for a laser handpiece according to one embodiment of the present invention.

FIG. 2 is a view to illustrate an application example of a tip 10 for a laser handpiece according to one embodiment of the present invention.

Referring to FIG. 2, the tip 10 for the laser handpiece according to one embodiment is attached to a handpiece 1. The handpiece 1 is a member that has a shape for a user to grip with a hand to radiate lasers onto a target T, and for example, in FIG. 2, a hand piece 1 of a gun shape is illustrated by way of an example. However, this shape is merely an example and the handpiece 1 may have a cylindrical shape as shown in FIG. 1 or other shapes.

An optical fiber or a light guiding arm may be connected to the handpiece 1, and lasers generated at a laser generator (for example, the laser generator 2 of FIG. 1) may be transmitted to the handpiece 1 through the optical fiber or the light guiding arm. The tip 10 for the laser handpiece for diagnosis according to one embodiment of the present disclosure may be coupled to an output side of the handpiece 1 for radiating lasers. The tip 10 for the laser handpiece for diagnosis may be configured to be attachable to or detachable from the handpiece 1, and may be attached to the handpiece 1 when necessary and may be detached therefrom when it is not necessary. In this case, the handpiece 1 may be used for original purposes, for example, for beauty care or medical care, when the tip 10 is not attached thereto.

One or more of a plurality of optical elements such as an optical fiber, a lens, a mirror, or the like, which are necessary for guiding lasers, may be arranged inside the handpiece 1. Light outputted from the handpiece 1 may be any one of a collimated beam, a focused beam or a defocused beam, and an energy density or a wavelength of a laser may vary according to a specific situation when a laser device is used.

As will be described below, the tip 10 for the laser handpiece for diagnosis according to the present invention may be configured to radiate a portion of a laser entering from the handpiece 1, rather than the entire laser, onto a target in order to easily make generated light while causing less thermal damage to the target.

That is, when the tip 10 for the laser handpiece for diagnosis according to the present invention is coupled to the handpiece 1, the tip 10 may radiate less laser energy per pulse onto the target than when a related-art laser handpiece tip (not shown) is coupled to the handpiece 1. That is, according to the present invention, the laser energy per pulse may be reduced and the density of laser energy per unit area may increase.

In addition, the tip 10 for the laser handpiece for diagnosis may be configured to, when radiating a laser onto the target T, radiate the laser onto the target in the form of a focused beam in order to easily make generated light.

The tip 10 for the laser handpiece for diagnosis according to the present invention as described above radiates a portion of the laser entering from the handpiece 1, rather than the entire laser, onto the target, and reduces a focus size (that is, a spot size) of the laser (for example, in the form of a focused beam) for the following reasons.

First, since the outputs of related-art laser devices for beauty care or treatment are very great (for example, 100-2000 mJ), the related-art laser devices may not be used as they are, for the purpose of diagnosing which is achieved by minimizing thermal damage and easily making generated light.

Secondly, the related-art laser devices for beauty care and treatment radiate lasers onto a large area of a skin surface (large spot size) in order to treat a largest skin area as quickly as possible. However, to be used for the purpose of diagnosing, the laser devices require a high density of energy per area in order to effectively make generated light without causing thermal damage, and this may not be achieved by the large spot size of the laser of the related-art devices.

Exemplary embodiments of the present invention are provided with a light adjusting module as described above. Hereinafter, other embodiments of the present invention provided with a light adjusting module will be described in detail with reference to the drawings.

Figure 3:
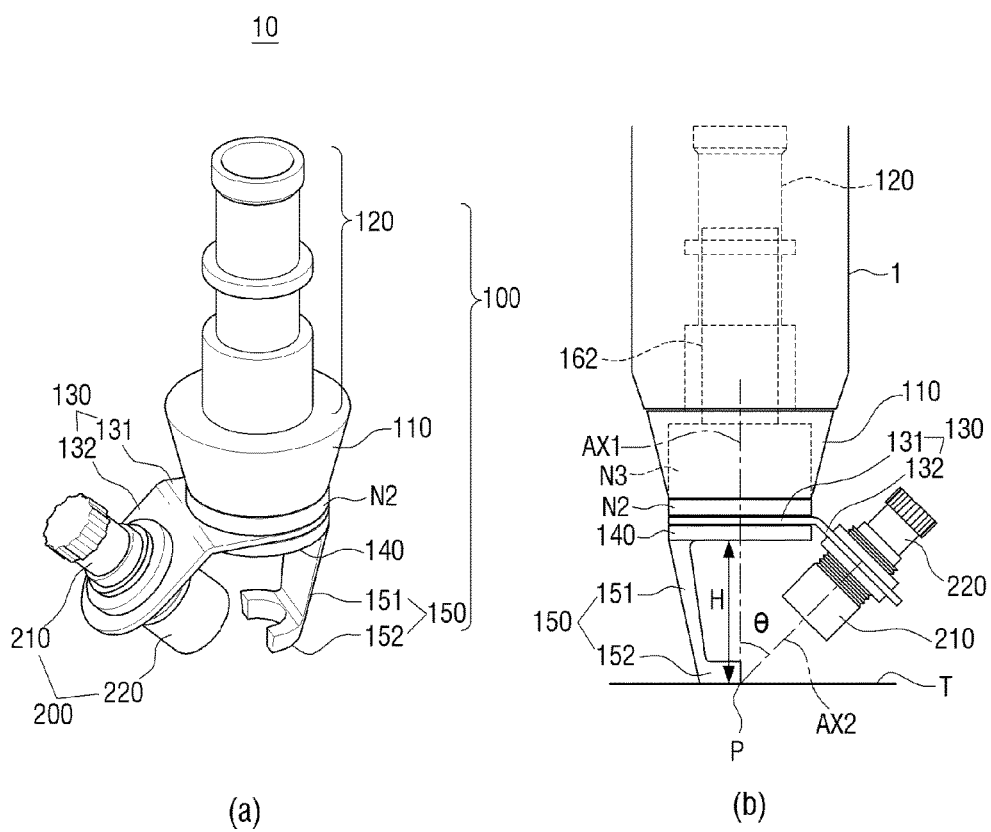
FIGS. 3, 4, and 5 are views to illustrate a tip for a laser handpiece according to a first embodiment.
Figure 4:
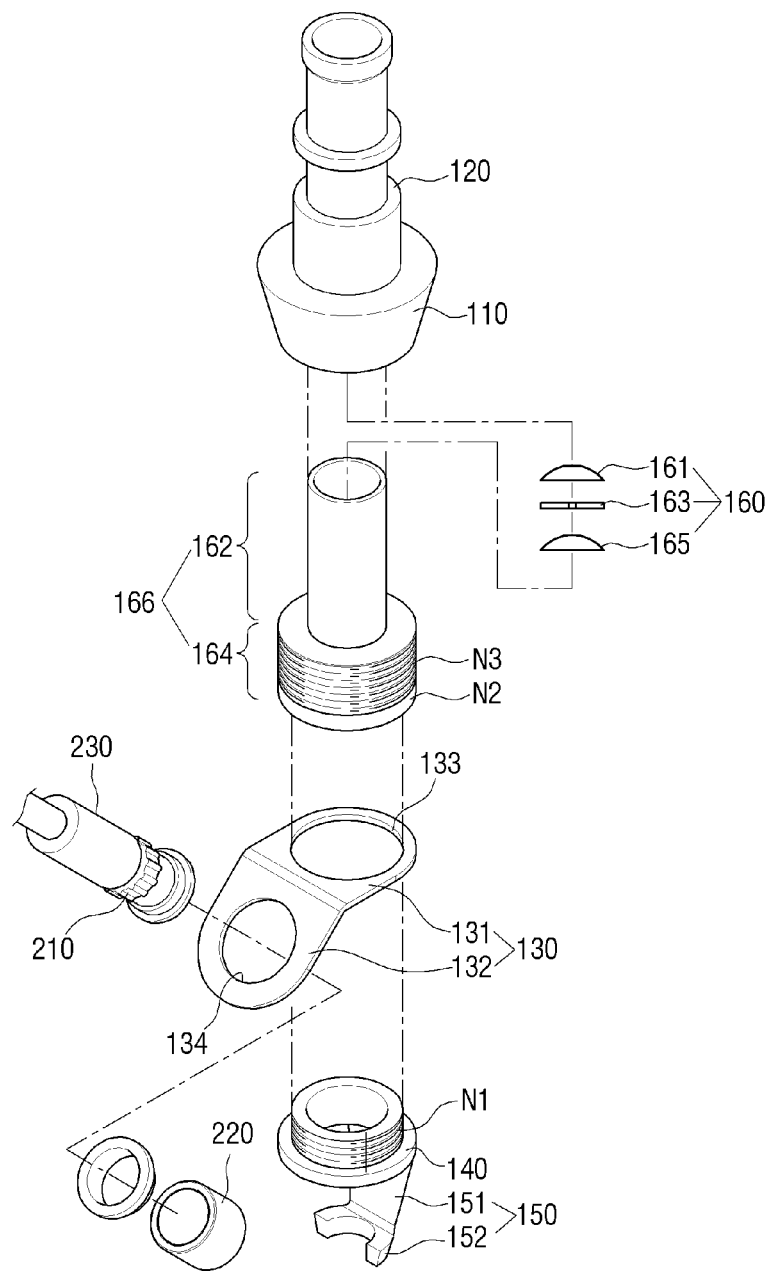
Figure 5:
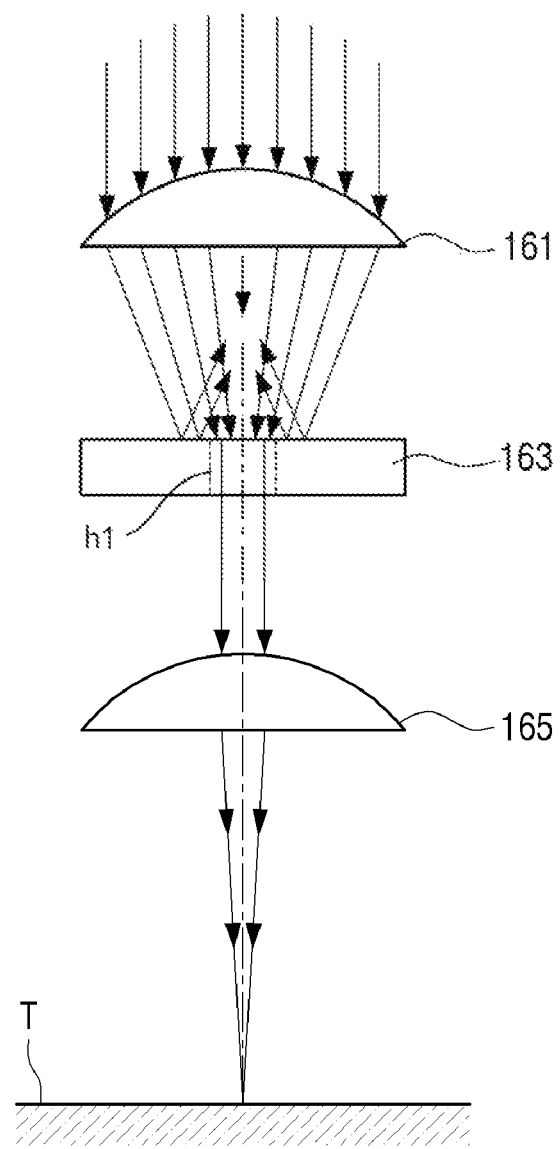

FIGS. 3, 4, and 5 are views to illustrate a tip 10 for a laser handpiece for diagnosis according to a first embodiment. FIG. 3(a) is a perspective view of the tip 10, FIG. 3(b) is a side view, FIG. 4 is an exploded perspective view, and FIG. 5 is a view to illustrate a light adjusting module 160.

Referring to the drawings, the tip 10 for the laser handpiece for diagnosis according to the first embodiment includes a light radiating module 100, a light receiving module 200, a light adjusting module 160, and a middle module 166.

The light radiating module 100 is a function module for radiating a laser toward a target T, and the light receiving module 200 is a module for receiving at least a portion of light which is generated by the laser radiated onto the target T, as received light.

The light adjusting module 160 is a module which is installed on a pathway of the laser moving toward the target T to adjust energy and a focus size of the laser radiated onto the target T.

For example, let's assume that, when a related-art handpiece tip (not shown) is coupled to the handpiece 1, energy per pulse of a laser radiated onto the target is about 50 mJ-1600 mJ, and a spot size of the laser is about 2 mm to 8 mm. In this case, when the light adjusting module 160 is coupled to the handpiece 1, energy per pulse of the laser radiated onto the target may be 20 mJ to 40 mJ and a spot size may be 100 µm to 500 µm. Herein, numerical values are merely examples and do not limit the scope of the present invention.

That is, due to the presence of the light adjusting module 160, a portion of the laser entering the tip 10 for the laser handpiece for diagnosis from the handpiece 1 is blocked and only a portion of the laser is radiated onto the target, and the spot size of the laser radiated onto the target is reduced.

In the following description, "light generated by a laser radiated onto a target" (hereinafter, referred to as "generated light") may refer to a certain kind of light which is generated when a laser is radiated onto a target, and for example, may refer to at least one of reflected light, scattered light, plasma light, and fluorescent light. The light receiving module 200 may receive at least a portion of the generated light as "received light."

In one embodiment, the light adjusting module 100 may include a base (main body) 110, a handpiece coupling portion 120, a module connecting portion 130, a fixing portion 140, and a guide portion 150. The base 110 may be a cylindrical member which has an inner space for allowing the laser outputted from the handpiece 1 to pass therethrough, and which is tapered such that its diameter is gradually reduced downward as in the illustrated embodiment.

The base 110 may have the inner space of the cylindrical shape formed therein to allow the laser to pass therethrough, and may have at least one of the optical elements such as a lens, an optical filter, a mirror, or the like arranged therein to adjust the focus size of the laser or filter a laser of an unnecessary wavelength.

The handpiece coupling portion 120 is a coupling member for coupling the base 110 and the handpiece 1 to each other. In the illustrated embodiment, the handpiece coupling portion 120 may have an inner space for allowing the laser to pass therethrough, and may be formed to extend from an upper portion of the base 110. In one embodiment, the base 110 and the handpiece coupling portion 120 may be integrally formed with each other. As schematically illustrated in FIG. 3(b), the handpiece coupling portion 120 is removably inserted into the handpiece 1, such that the tip 10 for the laser handpiece for diagnosis is removably coupled to the handpiece 1. In one embodiment, the handpiece coupling portion 120 may be coupled to the handpiece 1 in a tight-fitting method, or alternatively, may be coupled to the handpiece 1 in a well-known certain coupling method, such as a screwing method (for example, external screw threads are formed an outer surface of the handpiece coupling portion 120 and corresponding internal screw threads are formed on an inner surface of the handpiece 1).

The middle module 166 may have a cylindrical shape and have a hollow formed therein to allow the laser to move therethrough. In addition, the middle module 166 is formed in a cylindrical shape, and has an upper portion 162 coupled to the base 100 and a lower portion 164 coupled to the fixing portion 140.

The fixing portion 140 may be removably coupled to the lower portion 164 of the middle module 166, and the base 110 may be removably coupled to the upper portion 162 of the middle module 166.

In the present embodiment, the fixing portion 140 and the lower portion 164 of the middle module 166 may be coupled to each other in a well-known certain coupling method (for example, a tight-fitting method or a screwing method). For example, external screw threads N1 are formed on the outer surface of the fixing portion 140 and internal screw threads (not shown) corresponding to the external screw threads N1 are formed on the inner surface of the lower portion 164 of the middle module 166.

In the present embodiment, the base 110 and the upper portion 162 of the middle module 166 may be coupled to each other in a well-known certain coupling method (for example, a tight-fitting method or a screwing method). For example, external screw threads N3 are formed on the outer surface of the upper portion 162 of the middle module 166 and internal screw threads (not shown) corresponding to the external screw threads N3 are formed on the inner surface of the base 110.

In the present embodiment, the light adjusting module 160 may be positioned in the inner space (that is, a space in which the laser moves) of the middle module 166. The light adjusting module 160 is configured to allow only a portion of the laser entering from the handpiece 1 to pass therethrough and to reduce the focus size of the laser radiated onto the target.

The light adjusting module 160 includes a first lens 161, a plate 163 provided with a hole, and a second lens 165. Herein, the first lens 161 is an optional element, and according to an exemplary embodiment, the light adjusting module 160 may omit the first lens 161 and may include the plate 163 provided with the hole and the second lens 165. Hereinafter, a function of the light adjusting module 160 will be described in detail with reference to FIGS. 4 and 5.

The first lens 161 changes the spot size of the laser entering from the handpiece 1.

For example, the first lens 161 makes the spot size of the laser to be outputted to the plate 163 smaller than the spot size of the laser entering from the handpiece 1. In this example, the first lens 161 may be configured by a convex lens.

The plate 163 is provided with the hole h1 and allows the laser to pass through only the hole h1. That is, the plate 163 allows only a portion of the laser entering from the first lens 161 to pass therethrough.

For example, a diameter of the plate 163 is substantially identical to an inner diameter of the middle module 166, and the laser passing through the inside of the middle module 166 moves only through the hole provided in the plate 163.

The second lens 165 changes the spot size of the laser entering from the plate 163.

For example, the second lens 165 may change the spot size of the laser to be radiated onto the target to 100 μm to 500 μm. In this example, the second lens 165 may be configured by a convex lens.

The above-mentioned numerical values are merely examples and do not limit the scope of the present invention.

The light adjusting module 160 may not include the first lens 161 and may be configured to include the plate 163 provided with the hole and the second lens 165. According to an alternative embodiment, the light adjusting module 160 may be configured to reduce the intensity of the laser radiated toward the target. In this embodiment, the plate 163 may be replaced with a light reducing optical filter such as a neutral density filter, and thus the light adjusting module 160 can reduce the intensity of at least a portion of the laser.

The fixing portion 140 may be a member which is coupled to the inside of the lower portion of the middle module 166 to fix the module connecting member 130. In the illustrated embodiment, the fixing portion 140 may be coupled to a lower end of the middle module 166 and may have a shape having a hollow formed in the center thereof to allow the laser to pass therethrough. In one embodiment, the fixing portion 140 may have a cylindrical shape, and may have external screw threads N1 formed along the outer circumference of the upper portion thereof so as to be coupled to the middle module 166. However, the middle module 166 and the fixing portion 140 may be coupled to each other in one of various coupling methods such as a tight-fitting method, rather than the above-described screwing method.

The guide portion 150 may be formed at a lower portion of the fixing portion 140 to help a user easily align a center portion of the laser with a radiation point of the target. In the illustrated embodiment, the guide portion 150 may include a protruded guide 151 and a target contact portion 152.

The protruded guide 151 is a member which extends downward from the fixing portion 140 to a predetermined distance. The protruded guide 151 may be integrally formed with the fixing portion 140. When the protruded guide 151 is formed on the fixing portion 140, the user can easily adjust the handpiece so as to place the target T on the lower end of the protruded guide 151, and thus may position the target T at an appropriate distance from the handpiece.

In one embodiment, the target contact portion 152 may be formed at a lower end of the protruded guide 151. The target contact portion 152 is a member that is to be brought into contact with the target T, and may have an arc shape as shown in the drawings or a ring shape, or alternatively, may have a certain shape not to interfere with the laser radiated from the handpiece 1. When the target contact portion 152 has an arc or ring shape, the target contact portion 152 may be arranged such that the center axis of the laser outputted from the handpiece 1 is concentric with the center point of the arc or ring shape. In one embodiment, the fixing portion 10, the protruded guide 151, and the target contact portion 152 may be integrally formed with one another.

According to the above-described configuration of the guide portion 150, the user can easily align the center point of the target contact portion 152 and the radiation point of the target T with each other. Therefore, the user can position the target T at an appropriate distance from the handpiece 1 and may exactly radiate the laser outputted from the handpiece 1 onto the target T in focus.

In the above-described embodiment, the guide portion 150 is formed on the lower portion of the fixing portion 140, but the guide portion 150 may be omitted. In addition, the guide portion 150 may include only the protruded guide 151 and may omit the target contact portion 152.

The module connecting member 130 is a member that has a role of connecting the light radiating module 100 and the light receiving module 200. In the illustrated embodiment, the module connecting member 130 may be interposed between the middle module 166 and the fixing portion 140 and may be coupled to the light radiating module 100.

As shown in FIG. 4 in detail, the module connecting member 130 according to one embodiment is a member of a thin plate shape, and may include a first plate member 131 having a first penetrating hole 133 formed therein to allow the laser to pass therethrough, and a second plate member 132 having a second penetrating hole 134 formed therein to allow received light to pass therethrough. In this case, the second plate member 132 may be bent by a predetermined angle with respect to the first plate member 131.

The first plate member 131 is interposed and coupled between the middle module 160 and the fixing portion 140 of the light radiating module 100, and the second plate member 132 is coupled to the light receiving module 200.

The light receiving module 200 is a device that receives light generated from the target when the laser is radiated onto the target or right thereafter, as received light. In this case, the "generated light" may refer to reflected light, scattered light, plasma light, and/or fluorescent light, for example.

In the illustrated embodiment, the light receiving module 200 may include two pieces, that is, an upper piece 210 and a lower piece 220. Each of the upper piece 210 and the lower piece 220 may have a hollow formed therein to allow the received light to pass therethrough, and in the illustrated embodiment, each of the upper piece 210 and the lower piece 220 may have a cylindrical shape. The upper piece 210 and the lower piece 220 may be fastened to each other by screwing, and in this case, the second plate member 132 of the module connecting member 130 may be interposed and coupled between the upper piece 210 and the lower piece 220 of the light receiving module 200.

In one embodiment, an optical fiber 230 may be connected to an upper end of the upper piece 210 to transmit the received light to the outside (the optical fiber is omitted in FIG. 3). In addition, at least one optical element such as a lens, an optical filter, a mirror, or the like may be installed in any one of the upper piece 210 and the lower piece 220.

The second plate member 132 of the module connecting member 130 may be bent by a predetermined angle with respect to the first plate member 131, and the predetermined bending angle is determined to be an angle at which the light radiating module 100 and the light receiving module 200 are arranged to face the same point of the target T. That is, as shown in FIG. 3(b), when the center axis of the laser radiated from the light radiating module 100 is AX1 and the center axis of the received light received at the light receiving module 200 is AX2, the light radiating module 100 and the light receiving module 200 may be arranged such that the center axis AX1 of the laser and the center axis AX2 of the received light meet at a point P at which the target is placed (for example, a point which is distanced downward from the lower end of the base 110 by H), and the bending angle of the module connecting member 130 may be determined to meet such arrangement relationship.

Accordingly, since this arrangement relationship is met and thus only the light generated by the radiated laser is exactly received at the light receiving module 200, there is a low possibility that light generated by other factors is received, and a noise of the received light can be reduced.

According to the above-described configuration, the tip 10 for the laser handpiece for diagnosis may be implemented to have the light radiating module and the light receiving module integrated thereinto by coupling the light radiating module 100 and the light receiving module 200 through the module connecting member 130, and the generated light may be received simply by attaching the integration type tip 10 for the laser handpiece for diagnosis to the handpiece 1 without having to install a separate light receiving device.

In addition, the light radiating module 100 and the light receiving module 200 are integrated into the tip, but are arranged to face the same point of the target, such that there are advantages that the received light can be exactly received and a noise can be reduced.

Figure 6:
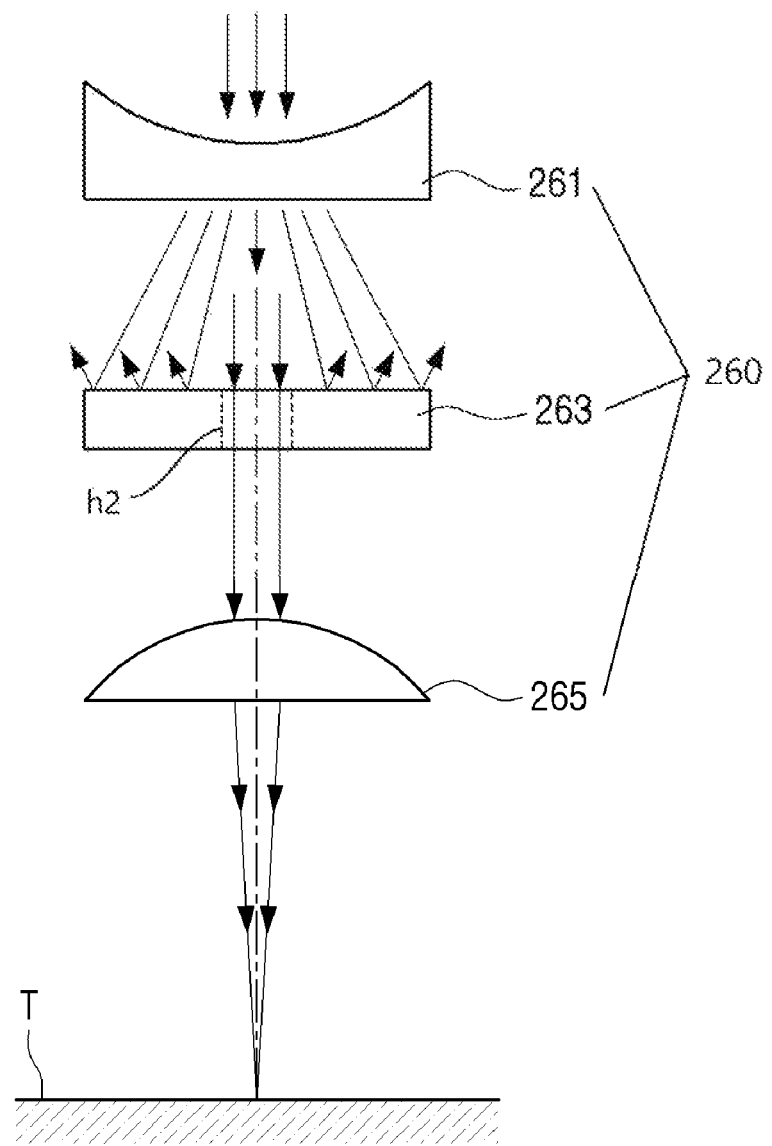
FIG. 6 is a view to illustrate a light adjusting module which is used in the tip for the laser handpiece according to one embodiment.

FIG. 6 is a view to illustrate a light adjusting module according to one embodiment of the present invention.

Referring to FIG. 6, the light adjusting module 260 may include a first lens 261, a plate 263 provided with a hole h2, and a second lens 265.

The light adjusting module 260 may be used in the tip 10 for the laser handpiece for diagnosis instead of the light adjusting module 160. The light adjusting module 160 or the light adjusting module 260 may be used according to a shape of a laser or output energy outputted from the handpiece 1 to which the tip 10 for the laser handpiece for diagnosis is coupled.

The light adjusting module 260 is positioned in the inner space (that is, a space in which the laser moves) of the middle module 166. The light adjusting module 260 may be configured to allow only a portion of the laser entering from the handpiece 1 to pass therethrough and to reduce a focus size of the laser radiated onto the target.

The first lens 261 changes the spot size of the laser entering from the handpiece 1. For example, the first lens 261 may be a concave lens and may change the focus size of the laser such that the spot size of the laser is the same as or similar to a diameter of the plate 263.

For example, the first lens 261 makes the spot size of the laser to be outputted toward the plate 263 larger than the spot size of the laser entering from the handpiece 1.

The plate 263 is provided with the hole h2 and the laser passes only through the hole h2. That is, the plate 263 allows only a portion of the laser entering from the lens 261 to pass therethrough.

For example, the diameter of the plate 263 is substantially identical to an inner diameter of the middle module 166, and thus the laser moving through the inside of the middle module 166 moves only through the hole h2 provided in the plate 263.

The second lens 265 change the spot size of the laser entering from the plate 263. For example, the second lens 265 may be a convex lens and may change the spot size of the laser to be radiated onto the target to 100 μm to 500 μm.

Herein, the numerical values are merely examples and do not limit the scope of the present invention.

According to one embodiment, the light adjusting module 260 may not include the first lens 261 and may be configured to include the plate 263 provided with the hole and the second lens 265. According to an alternative embodiment, the light adjusting module 260 may be configured to reduce the intensity of the laser radiated toward the target. For example, the plate 263 may be replaced with a light reducing optical filter such as a neutral density filter, and thus the light adjusting module 260 can reduce the intensity of at least a portion of the laser.

Figure 7:
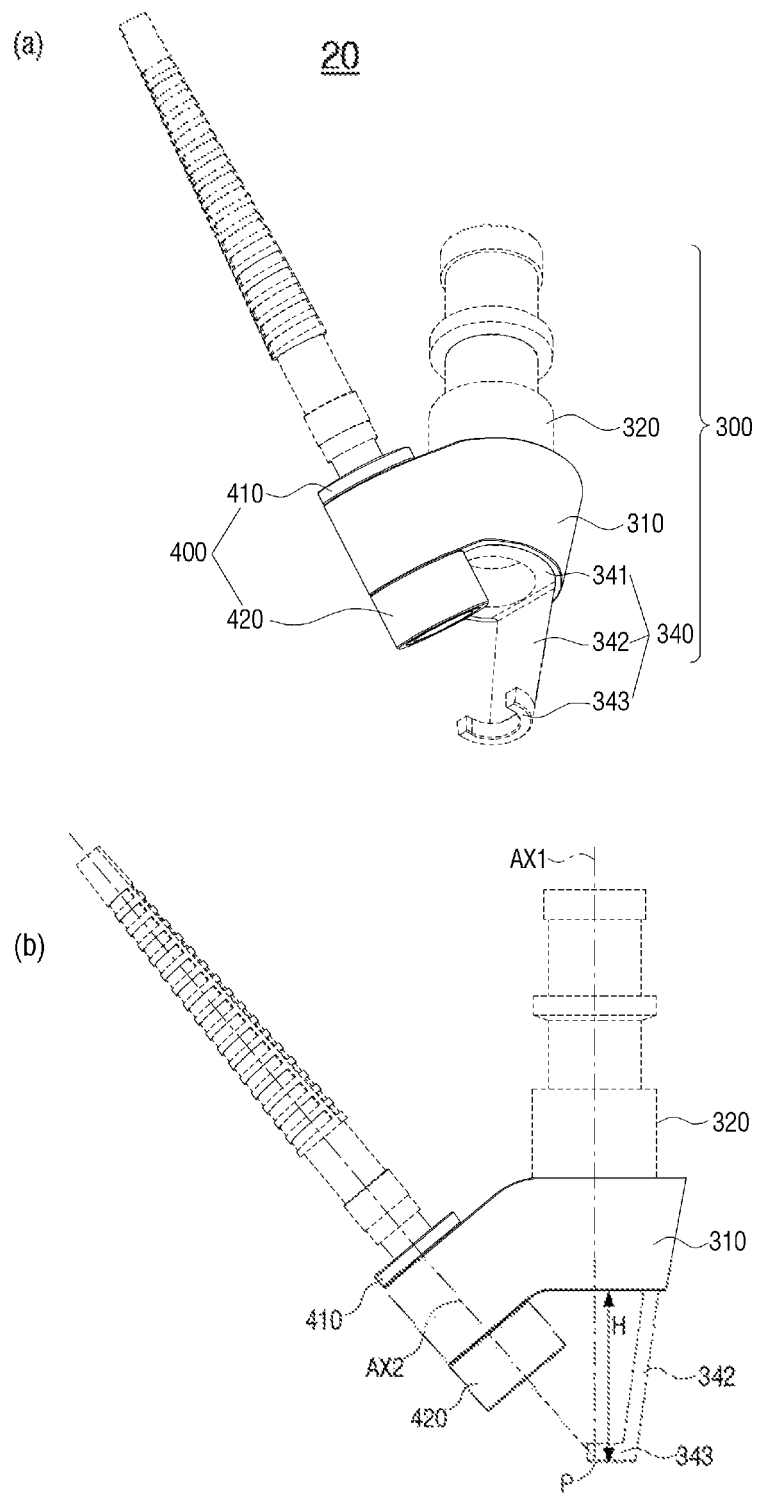
FIGS. 7, 8, and 9 are views to illustrate a tip for a laser handpiece according to a second embodiment.
Figure 8:
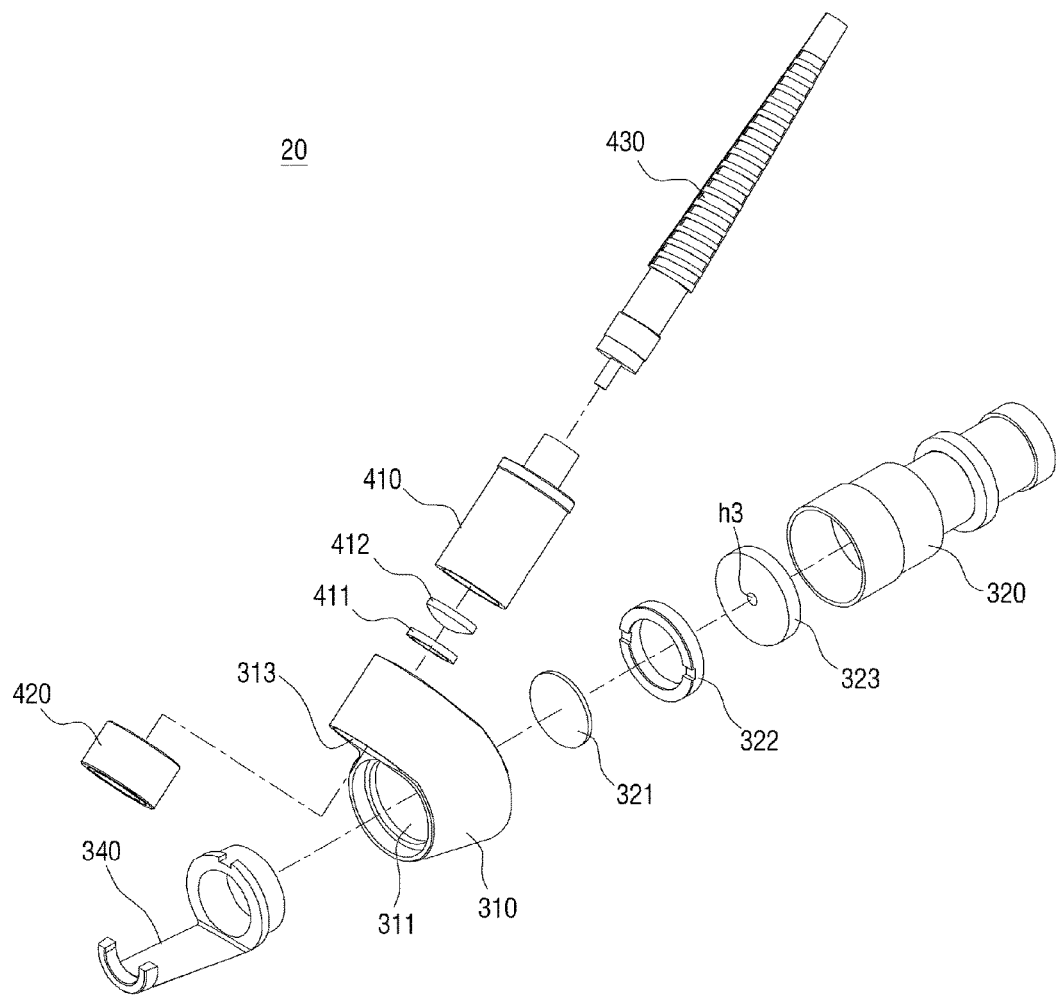
Figure 9:
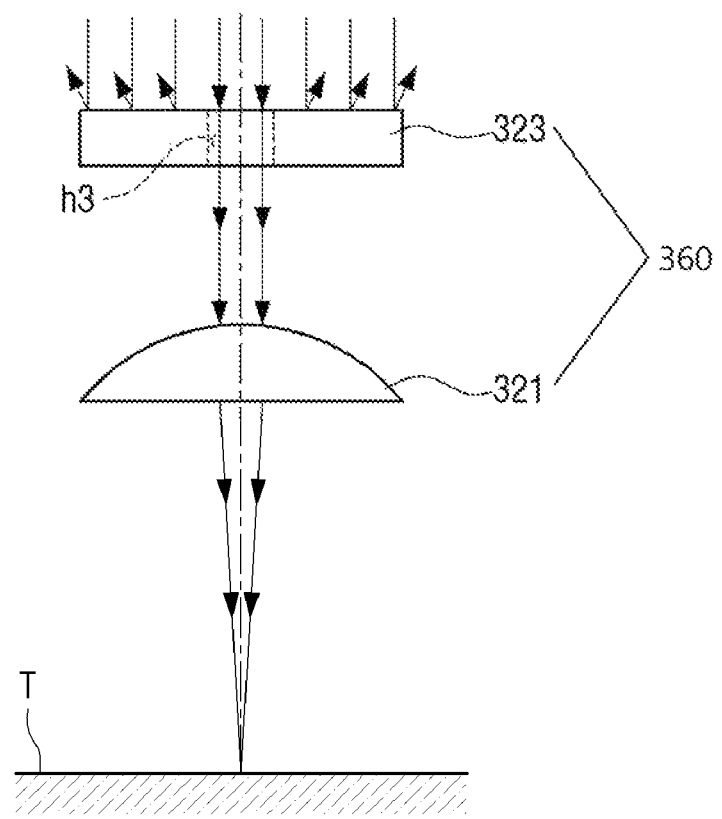

A tip 20 for a laser handpiece for diagnosis according to a second embodiment will be described with reference to FIGS. 7, 8, and 9. FIGS. 7 and 8 illustrate the tip 20 for the laser handpiece for diagnosis according to the second embodiment, and FIG. 7(a) is a perspective view of the tip 20, FIG. 7(b) is a side view, FIG. 8 is an exploded perspective view, and FIG. 9 is a view to illustrate a light adjusting module 360.

Referring to these drawings, the tip 20 for the laser handpiece for diagnosis according to the second embodiment may include a light radiating module 300 and a light receiving module 400, and the light radiating module 300 may include the light adjusting module. Herein, the light radiating module 300 is a module for radiating a laser onto the target T, and the light receiving module 400 is a module for receiving at least a portion of generated light which is generated by the laser radiated onto the target T, as received light. The light adjusting module is a module that is installed on a pathway of the laser moving toward the target T to adjust energy and a focus size of the laser radiated onto the target T.

As will be described below, the tip 20 for the laser handpiece for diagnosis according to the present invention may be configured to radiate a portion of the laser entering from the handpiece 1 onto the target in order to easily make the generated light while causing less thermal damage to the target when the laser is radiated onto the target.

That is, when the tip 20 for the laser handpiece for diagnosis according to the present invention is coupled to the handpiece 1, the tip 20 may radiate less laser energy per pulse onto the target than when a related-art laser handpiece tip (not shown) is coupled to the handpiece 1. In addition, the tip 20 for the laser handpiece for diagnosis may be configured to output a focused beam to the target to easily make the generated light.

In one embodiment, the light radiating module 300 may include a base 310, a handpiece coupling portion 320, and a guide portion 340. Compared with the tip 10 for the laser handpiece for diagnosis according to the first embodiment of FIGS. 3 and 4, the tip 20 for the handpiece according to the second embodiment differs from the tip 10 in that the base 310 also has a role of the module connecting member 130 of the tip 10 of the first embodiment. That is, in the tip 20 for the handpiece according to the second embodiment, the light radiating module 300 and the light receiving module 400 are coupled to each other through the base 310 and a separate module connecting member 130 is not required. In the embodiment shown in FIGS. 7 and 8, the base 310 may have a first inner space 311 to allow the laser to pass therethrough and a second inner space 313 to allow received light to pass therethrough. Each of the first inner space 311 and the second inner space 313 may have a cylindrical shape or a tapered cylindrical shape having its diameter gradually reduced downward.

The handpiece coupling portion 320 is a coupling member for coupling the base 310 and the handpiece 1 to each other. In the illustrated embodiment, the handpiece coupling portion 320 may be a cylindrical shape having an inner space to allow the laser to pass therethrough. The base 310 and the handpiece coupling portion 320 may be separately manufactured and combined with each other. In the illustrated embodiment, the handpiece coupling portion 320 may be coupled to the base 310 by having a portion of the lower portion thereof at least partially inserted into the first inner space 311 of the base 310, and may be coupled to the handpiece 1 by having a portion of the upper portion of the handpiece coupling portion 320 removably inserted into the handpiece 1. Alternatively, the handpiece coupling portion 320 may be formed to extend from the upper portion of the base 310 and may be integrally formed with the base 310. In one embodiment, the handpiece coupling portion 320 may be coupled to the handpiece 1 in a well-known method such as a tight-fitting method or a screwing method.

The light adjusting module 360 is arranged in an inner space of at least one of the base 310 and the handpiece coupling portion 320.

The light adjusting module 360 performs operations of adjusting the focus size of the laser and blocking a portion of the laser.

In one embodiment, the light adjusting module 360 includes a plate 323 for blocking a portion of the laser and a lens 321 for adjusting the focus size of the laser.

Referring to FIG. 9, the plate 323 is provided with a hole h3 and the laser may pass through only the hole h3. That is, the plate 323 allows only a portion of the laser entering from the handpiece 1 to pass therethrough.

When the plate 323 is configured to be positioned in the base 310, a diameter of the plate 323 may be substantially identical to an inner diameter of the base 310, and accordingly, the laser moving through the inside of the base 310 moves toward the target T only through the hole provided in the plate 323.

On the other hand, when the plate 323 is configured to be positioned in the handpiece coupling portion 320, the diameter of the plate 323 may be substantially identical to an inner diameter of the handpiece coupling portion 320, and accordingly, the laser moving through the inside of the handpiece coupling portion 320 moves toward the target T only through the hole h3 provided in the plate 323.

In the above-described embodiments, a size of the hole h3 formed in the plate 323 may be determined such that energy per pulse of the laser radiated onto the target T has a desired value. For example, the size of the hole formed in the plate 323 may be determined such that energy per pulse of the laser radiated onto the target T is 20 mJ to 40 mJ. Herein, the numerical values are merely examples and do not limit the scope of the present disclosure.

The lens 321 changes the spot size of the laser entering from the plate 323. For example, the lens 321 may change the spot size of the laser to be radiated onto the target to 100 μm to 500 μm. According to the present embodiment, the lens 321 may be configured by a convex lens.

According to an alternative embodiment, the light adjusting module 360 may be configured to reduce the intensity of the laser radiated toward the target. For example, the plate 323 may be replaced with a light reducing optical filter such as a neutral density filter, and thus the light adjusting module 360 can reduce the intensity of at least a portion of the laser.

The above-described numerical values are merely example and do not limit the scope of the present invention.

The guide portion 340 may be attached to a lower portion of the base 310. The guide portion 340 is a device which is selectively attached to allow the user to easily align a center point of the laser with the target T1, and, in the illustrated embodiment, the guide portion 340 may include a connecting portion 341, a protruded guide 342, and a target contact portion 343. The connecting portion 341 is a member which is coupled to the lower portion of the base 310, and has a hollow inner space formed therein to allow the laser to pass therethrough. In one embodiment, the connecting portion 341 may have external screw threads formed along the outer circumference of an upper portion thereof so as to be coupled to the base 310 in a screwing method. In an alternative embodiment, the connecting portion 341 may have a coupling structure to be coupled in one of various well-known coupling method such as a tight-fitting method or the like. The structures and functions of the protruded guide 342 and the target contact portion 343 are the same as or similar to those of the protruded guide 151 and the target contact portion 152 in the first embodiment described above with reference to FIGS. 3 and 4, and thus a detailed description thereof is omitted.

Although it is illustrated that the guide portion 340 includes both the protruded guide 342 and the target contact portion 343, the target contact portion 343 may be omitted in an alternative embodiment.

In the illustrated embodiment, the light receiving module 400 may include an upper piece 410 and a lower piece 420. Each of the upper piece 410 and the lower piece 420 may have a cylindrical shape having a hollow space formed therein to allow received light to pass therethrough.

In one embodiment, an optical fiber 430 may be connected to an upper end of the upper piece 410 to transmit the received light to the outside. In addition, at least one optical element such as a lens 412, an optical filter, a mirror, or the like may be installed inside at least one of the upper piece 410 and the lower piece 420.

The upper piece 410 of the light receiving module 400 may be at least partially inserted into and coupled to the second inner space 313 of the base 310 of the light radiating module 300. The lower piece 420 of the light receiving module 400 may be coupled to a lower end of the upper piece 410 or a lower end of the second inner space 313 of the base 310. Coupling between the upper piece 410 and the base 310 and coupling between the lower piece 420 and the base 310 or the upper piece 410 may be implemented in a well-known method, for example, a tight-fitting method or a screwing method.

The first inner space 311 and the second inner space 313 of the base 310 may not be parallel to each other and may be titled to form an angle therebetween, and preferably, the first and second inner spaces 311 and 313 of the base 310 may be arranged such that the light radiating module 300 and the light receiving module 400 are arranged to face the same point of the target T. That is, as shown in FIG. 7(b), the light radiating module 300 and the light receiving module 400 may be arranged such that the center axis AX1 of the laser radiated from the light radiating module 300 and the center axis AX2 of the received light received at the light receiving module 400 meet at a point (P) where the target T is placed (for example, a point distanced downward from the lower end of the base 310 by H), and the base 310 is configured to meet this arrangement relationship.

Figure 10:
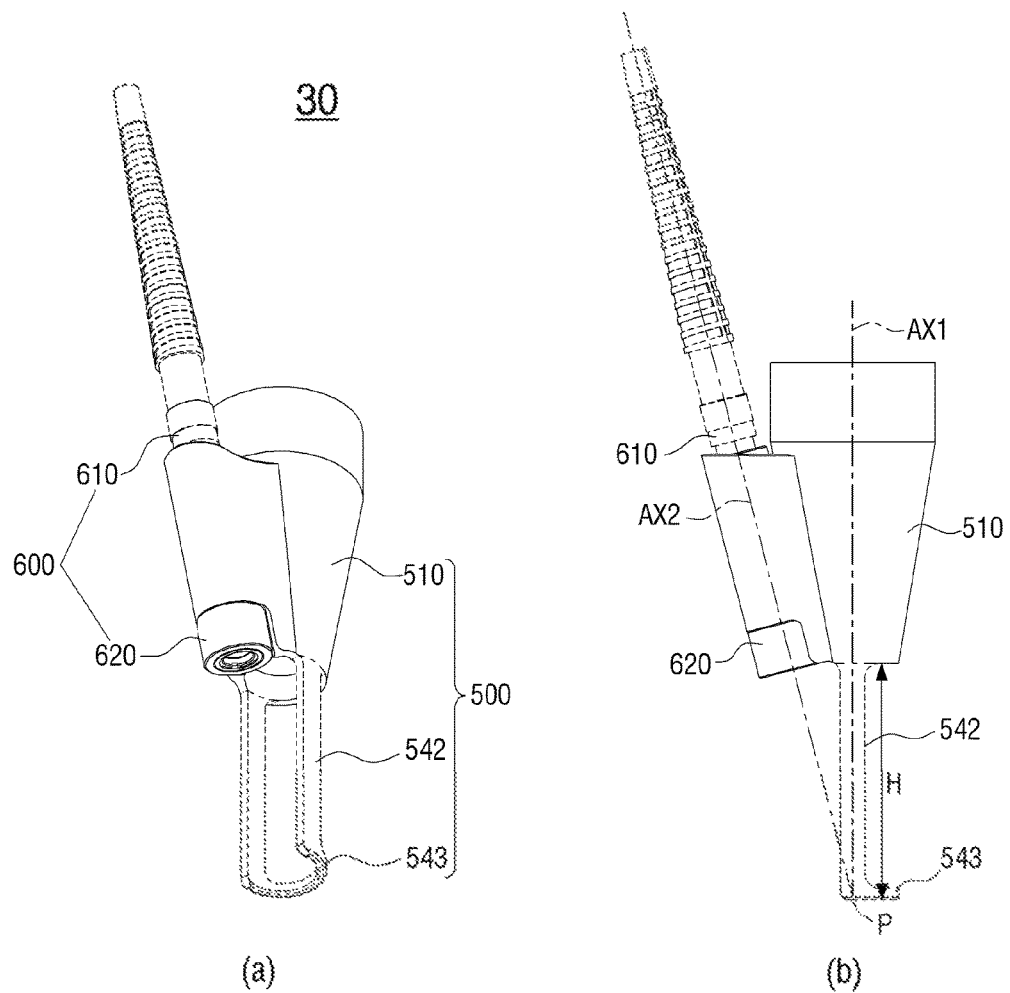
FIGS. 10 and 11 are views to illustrate a tip for a laser handpiece according to a third embodiment.
Figure 11:
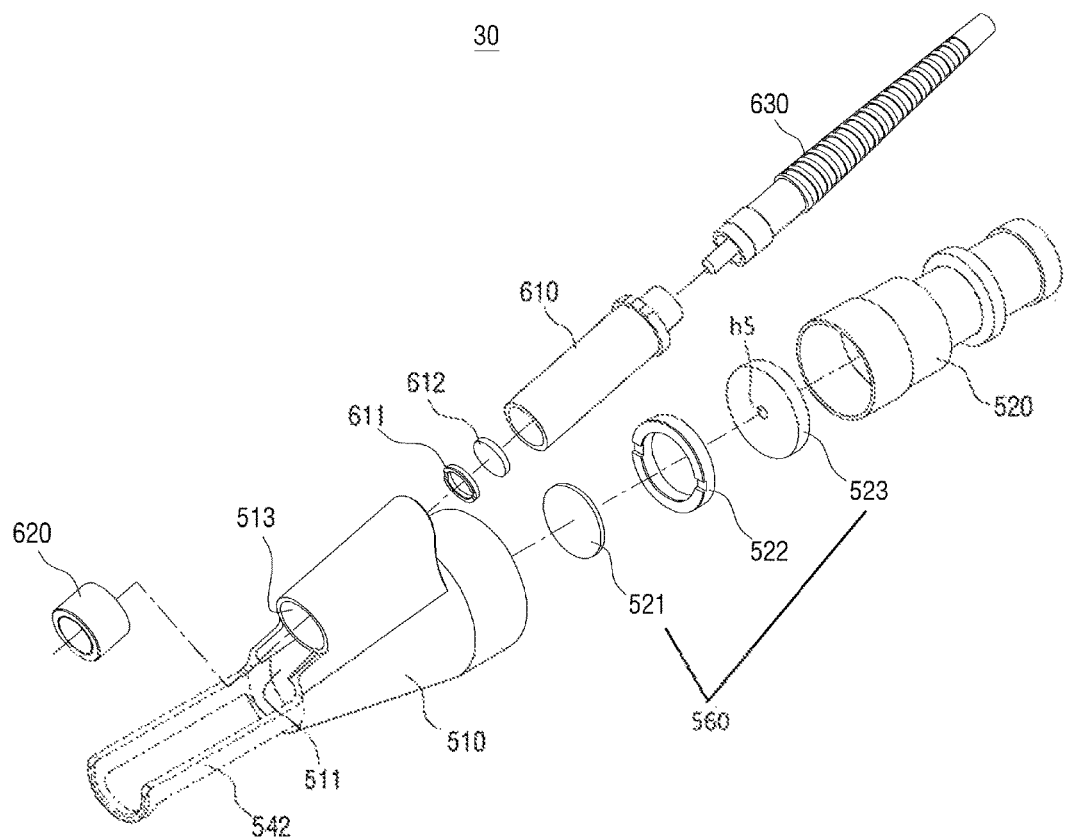

A tip 30 for a laser handpiece for diagnosis according to a third embodiment will be described with reference to FIGS. 10 and 11. FIGS. 10 and 11 illustrate the tip 30 for the laser handpiece for diagnosis according to the third embodiment, and FIG. 10(a) is a perspective view of the tip 30, FIG. 10(b) is a side view, and FIG. 11 is an exploded perspective view.

Referring to the drawings, the tip 30 for the laser handpiece for diagnosis according to the third embodiment may include a light radiating module 500 and a light receiving module 600, and the light radiating module 500 may include a light adjusting module 560. The light radiating module 500 includes a base 510 and guide portions 542 and 543. The light radiating module 500 may further include a handpiece connecting portion (not shown) although it is not illustrated.

The light adjusting module is a module that is installed on a pathway of the laser moving toward the target T to adjust energy and a focus size of the laser radiated onto the target T.

In the present embodiment, the light adjusting module 560 may include a plate 523 provided with a hole h5 and a lens 521. Herein, the plate 523 has the same function as that of the plate 323 or the plate 163 described above with reference to other drawings, and the lens 521 has the same function as that of the lens 165 or the lens 321.

As will be described below, the tip 30 for the laser handpiece for diagnosis according to the present invention may be configured to radiate a portion of the laser entering from the handpiece 1 onto the target in order to easily make the generated light while causing less thermal damage to the target.

That is, when the tip 30 for the laser handpiece for diagnosis according to the present invention is coupled to the handpiece 1, laser energy per pulse radiated onto the target is less than energy per pulse when a related-art laser handpiece tip (not shown) is coupled to the handpiece 1, but a density of energy per unit area is greater than that of the related-art tip. In addition, the tip 30 for the laser handpiece for diagnosis may be configured to output a laser having a small focus size, such as a focused beam, to the target to increase the density of energy per unit area with low energy and thus to easily make the generated light.

Compared with the tip 20 for the laser handpiece for diagnosis according to the second embodiment of FIGS. 7 and 8, the tip 30 for the laser handpiece for diagnosis according to the third embodiment differs from the tip 20 in that the guide portion is integrally formed with the base 510. That is, in the tip 30 for the laser handpiece for diagnosis according to the third embodiment, a protruded guide 542 directly extends from a lower end of the base 510 and a target contact portion 543 is integrally formed with a lower end of the protruded guide 542.

The base 510 may include a first inner space 511 to allow the laser to pass therethrough, and a second inner space 513 to allow received light to pass therethrough, and a handpiece connecting portion (not shown) may be inserted into and coupled to the first inner space 511 in part, and the light receiving module 600 may be connected to the second inner space 513. The light receiving module 600 may include an upper piece 610 and a lower piece 620.

In the present embodiment, the light adjusting module 560 is arranged in an inner space of at least one of the base 510 and a handpiece coupling portion 520.

The light adjusting module 560 performs an operation of adjusting the focus size of the laser or blocking a portion of the laser.

In one embodiment, the light adjusting module 560 includes the plate 523 to block a portion of the laser, and the lens 521 to adjust the focus size of the laser.

In the present embodiment, the plate 523 is provided with the hole h5 and the laser passes only through the hole h5.

That is, the plate 523 allows only a portion of the laser entering from the handpiece 1 to pass therethrough.

When the plate 523 is configured to be positioned in the base 510, a diameter of the plate 523 may be substantially identical to an inner diameter of the base 310, and accordingly, the laser moving through the inside of the base 510 moves toward the target T only through the hole provided in the plate 523.

On the other hand, when the plate 523 is configured to be positioned in the handpiece coupling portion 520, the diameter of the plate 523 may be substantially identical to an inner diameter of the handpiece coupling portion 520, and accordingly, the laser moving through the inside of the handpiece coupling portion 520 moves toward the target T only through the hole provided in the plate 523.

In the above-described embodiments, a size of the hole h5 formed in the plate 523 may be determined such that energy per pulse of the laser radiated onto the target T has a desired value. For example, the size of the hole formed in the plate 523 may be determined such that energy per pulse of the laser radiated onto the target T is 20 mJ to 40 mJ. Herein, the numerical values are merely examples and do not limit the scope of the present disclosure.

The lens 521 changes the spot size of the laser entering from the plate 523. For example, the lens 521 may change the spot size of the laser to be radiated onto the target to 100 μm to 500 μm. Herein, the numerical values are merely examples and do not limit the scope of the present disclosure.

The configurations of the light radiating module 500 and the light receiving module 600 are the same as or similar to the light radiating module 300 and the light receiving module 400 of the tip 20 for the handpiece according to the second embodiment, and thus a detailed description thereof is omitted.

Figure 12:
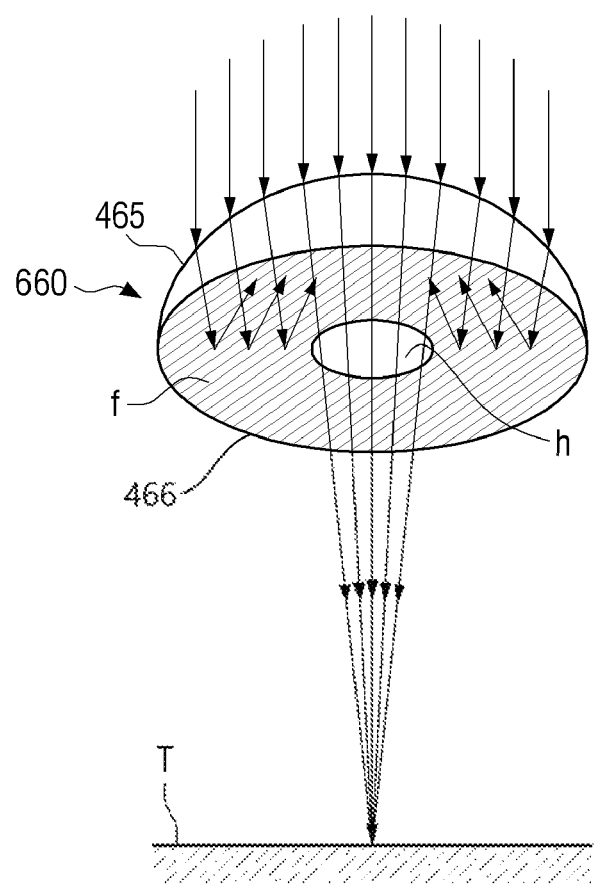
FIG. 12 is a view to illustrate a light adjusting module which is used in the tip for the laser handpiece according to one embodiment.

FIG. 12 is a view to illustrate a light adjusting module which is used in a tip for a laser handpiece for diagnosis according to the present invention.

Referring to FIG. 12, the light adjusting module 660 which is used in a tip for a laser handpiece for diagnosis according to the present invention is illustrated by way of an example.

The light adjusting module 660 performs an operation of adjusting a focus size of a laser or blocking a portion of a laser.

According to the present embodiment, the light adjusting module 660 is configured by a convex lens having a blocking layer f for blocking lasers. The blocking layer f may be made of any material that can prevent lasers from passing therethrough. For example, metal which can reflect lasers may be used for the blocking layer f.

A region n may be formed on the substantially center of the light adjusting module 660 to allow lasers to pass therethrough, and lasers may be outputted to the outside through the region n.

According to the present invention, the light adjusting module 660 may be configured by a hemispherical convex lens, and the hemispherical convex lens may include a round portion 465 to receive lasers and a flat surface portion 466 to output lasers. The flat surface portion 466 includes the blocking layer f for blocking lasers and the region n for allowing lasers to pass therethrough.

The light adjusting module 660 is used in the tip for the laser handpiece for diagnosis according to the present invention.

For example, the light adjusting module 660 may be used in the tip 30 for the laser handpiece for diagnosis described above with reference to FIGS. 10 and 11. That is, the light adjusting module 660 may be used instead of the light adjusting module 560 of the tip 30 for the laser handpiece for diagnosis.

In another example, the light adjusting module 660 may be used in the tip 20 for the laser handpiece for diagnosis described above with reference to FIG. 8. That is, the light adjusting module 660 may be used instead of the light adjusting module 360 of the tip 20 for the laser handpiece for diagnosis.

In still another example, the light adjusting module 660 may be used in the tip 10 for the laser handpiece for diagnosis described above with reference to FIG. 4. That is, the light adjusting module 660 may be used instead of the light adjusting module 160 of the tip 10 for the laser handpiece for diagnosis. For example, the light adjusting module 660 may be used instead of the plate 163 and the second lens 165.

In yet another example, the light adjusting module 660 may be used instead of the light adjusting module 260 described above with reference to FIG. 6. For example, the light adjusting module 660 may be used instead of the plate 263 and the second lens 265.

According to the above-described embodiments, an energy spectrum of a related-art laser device for skin treatment and beauty care is not required to be separately changed, and, simply by replacing the tip for the handpiece according to the present invention, lasers used for skin treatment and beauty care may be directly utilized for the purpose of disease diagnosis.

Figure 13:
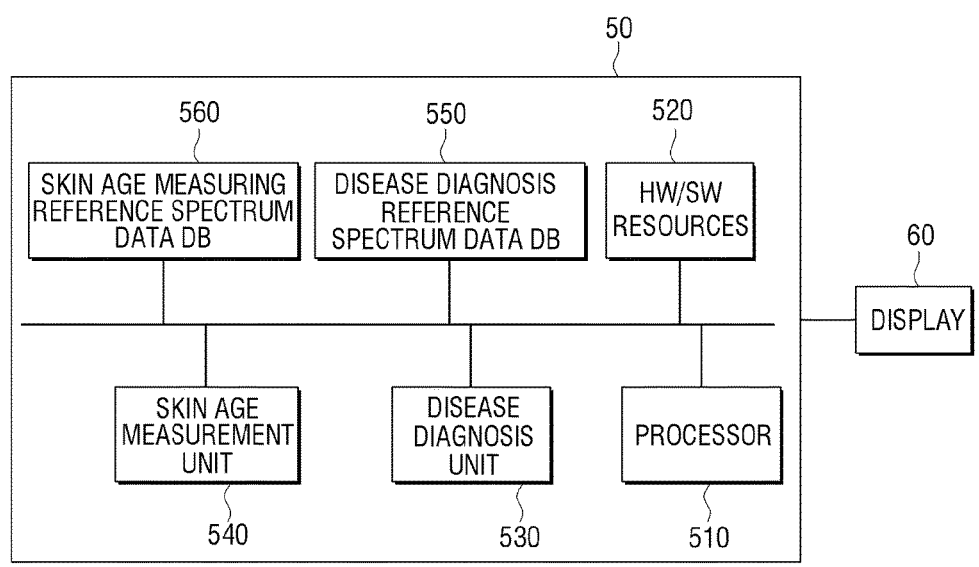
FIG. 13 is a view to illustrate an example of a configuration of a data processing unit according to one embodiment.

FIG. 13 is a view to illustrate an example of a configuration of a data processing unit according to one embodiment. Referring to FIG. 13, the data processing unit 50 is an element which is substituted for the data processing unit 5 of the related-art device of FIG. 1. That is, the received light which is received through the tip 10, 20, 30 for the laser handpiece for diagnosis described above with reference to FIGS. 2 to 12 may be transmitted to the data processing unit 50 through a spectrometer.

According to one embodiment, the data processing unit 50 may include a processor 510 and other hardware/software resources 520, and may further include a disease diagnosis unit 530, a skin age measurement unit 540, a disease diagnosis reference spectrum data DB 550, and a skin age measuring reference spectrum data DB 560 for diagnosing a disease or measuring a skin age by analyzing received light.

For example, the hardware/software resources 520 may include a memory (not shown), a storage unit (not shown) which is able to store and read data, image processing software (not shown) and hardware (not shown) for processing images to be displayed on a display 60, voice processing software (not shown) and hardware (not shown), transmitters and receivers (not shown) for transmitting and receiving data to or from the outside, and programs for operating the respective elements.

The processor 510 controls the elements of the data processing unit 50, for example, the hardware/software resources 520, the disease diagnosis unit 530, the skin age measurement unit 540, the disease diagnosis reference spectrum data DB storage 550, and the skin age measurement reference spectrum data DB storage 560, to perform their respective operations.

The disease diagnosis unit 530 may determine whether there is a disease in the body tissue based on a measured spectrum of the received light with reference to the disease diagnosis reference spectrum data DB 550. For example, the disease diagnosis unit 530 may determine whether there is a disease by comparing the spectrum of the received light and the disease diagnosis reference spectrum data DB 550

The skin age measurement unit 540 may measure a skin angle based on a measured spectrum of the received light with reference to the skin age measurement reference spectrum data DB 560. For example, the skin age measurement unit 540 may measure the skin age by comparing a spectrum of generated light measured by a spectrometer, and the skin age measurement reference spectrum data DB 560. The skin age measurement unit 540 may identify a component for measuring the skin age based on the spectrum of the received light. The component for measuring the skin age may be collagen, for example.

According to one embodiment, the skin age measurement reference spectrum data DB 560 may be a DB including data having an amount of collagen and a skin age matched with each other. In this embodiment, the skin age measurement unit 540 may identify an amount of collagen based on the spectrum of the received light, and may measure a skin angle by referring to the skin age measurement reference spectrum data DB. The result of diagnosing by the disease diagnosis unit 540 and the result of measuring by the skin age measurement unit 560 may be displayed on the display 60.

In the illustrated embodiment, a disease may be diagnosed or a skin age may be measured by analyzing the received light which is received through the tip 10, 20, 30 for the laser handpiece for diagnosis. However, data processing may be performed based on the received light for other purposes or other uses.

While the invention has been shown and described with reference to certain preferred embodiments thereof and the drawings, the present invention is not limited to the above-described embodiments, and various modifications or other embodiments which belong to the equivalents of the scope of the present invention can be achieved by a person skilled in the art.

EXPLANATION OF REFERENCE NUMBERS

1: Handpiece
10, 20, 30: Tip for laser handpiece
100, 300, 500: Light radiating module
200, 400, 600: Light receiving module

What is claimed is:

1. A tip for a laser handpiece, comprising:
a light radiating module configured to radiate a laser toward a target; and
a light receiving module configured to receive at least a portion of light which is generated by the laser radiated onto the target as received light,
wherein the light radiating module comprises:
a base which has an inner space formed therein to allow the laser to pass therethrough;
a fixing portion which is coupled to a lower portion of the base and has a penetrating hole formed therein to allow the laser to pass therethrough; and
a module connecting member which is interposed and fixed between the base and the fixing portion, and
wherein the light receiving module is coupled to the module connecting member, such that the light radiating module and the light receiving module are integrally coupled to a laser handpiece.

2. The tip of claim 1, wherein the light radiating module and the light receiving module are arranged such that a center axis of the laser and a center axis of the received light meet at a point where the target that the laser is radiated onto is placed.

3. The tip of claim 1, wherein the light radiating module further comprises a handpiece coupling portion which has an inner space formed therein to allow the laser to pass therethrough, and is formed on an upper portion of the base and is removably coupled to the handpiece by being inserted into the handpiece.

4. The tip of claim 1, wherein the fixing portion comprises a protruded guide which extends downward to a predetermined distance.

5. The tip of claim 1, wherein the module connecting member comprises a first plate member having a first penetrating hole formed therein to allow the laser to pass therethrough, and a second plate member having a second penetrating hole formed therein to allow the received light to pass therethrough, and the second plate member is bent by a predetermined angle with respect to the first plate member.

6. The tip of claim 5, wherein the first plate member is interposed and coupled between the base of the light radiating module and the fixing portion, and the second plate member is coupled to the light receiving module.

7. The tip of claim 1, further comprising a light adjusting module which is arranged on a pathway of the laser moving toward the target,
wherein the light adjusting module is configured to block or reduce at least a portion of the laser radiated toward the target.

8. The tip of claim 7, wherein the light adjusting module is also configured to adjust a focus size of the laser radiated toward the target.

9. The tip of claim 7, wherein the light adjusting module comprises a plate provided with a hole or a light reducing optical filter.

10. The tip of claim 8, wherein the light adjusting module comprises a plate provided with a hole or a light reducing optical filter, and a lens for adjusting the focus size of the laser.

11. The tip of claim 8, wherein the light adjusting module is a convex lens which adjusts the focus size of the laser radiated toward the target, and the convex lens has a blocking layer for blocking a portion of the laser.

12. A tip for a laser handpiece, comprising:
a light radiating module configured to radiate a laser toward a target; and
a light receiving module configured to receive at least a portion of light which is generated by the laser radiated onto the target as received light,
wherein the light radiating module comprises a base which has a first inner space to allow the laser to pass therethrough and a second inner space to allow the received light to pass therethrough,
wherein the light receiving module is coupled to the base of the light radiating module such that the light radiating module and the light receiving module are integrally coupled to a laser handpiece.

13. The tip of claim 12, wherein the light receiving module comprises:
a first piece which has a cylindrical shape and has an inner space to allow the received light to pass therethrough; and
a second piece which has an inner space to allow the received light to pass therethrough, and is fastened to a lower end of the first piece or a lower end of the second inner space of the base.

14. The tip of claim 13, wherein the first piece of the light receiving module is at least partially inserted into the second inner space of the base of the light radiating module, and the second piece is fastened to the lower end of the first piece or the lower end of the second inner space of the base, such that the light receiving module is coupled to the light radiating module.

15. The tip of claim 12, wherein the light radiating module and the light receiving module are arranged such that a center axis of the laser and a center axis of the received light meet at a point where the target that the laser is radiated onto is placed.

16. The tip of claim 12, wherein the light radiating module further comprises a handpiece coupling portion which has a cylindrical shape and has an inner space formed therein to allow the laser to pass therethrough, and
wherein the handpiece coupling portion is coupled to the light radiating module by having a portion thereof at least partially inserted into the first inner space of the base of the light radiating module, and the handpiece coupling portion is removably coupled to the handpiece by having the other portion thereof inserted into the handpiece.

17. The tip of claim 12, further comprising a light adjusting module which is arranged on a pathway of the laser moving toward the target,
wherein the light adjusting module is configured to block or reduce at least a portion of the laser radiated toward the target.

18. The tip of claim 17, wherein the light adjusting module is also configured to adjust a focus size of the laser radiated toward the target.

19. The tip of claim 17, wherein the light adjusting module comprises a plate provided with a hole or a light reducing optical filter.

20. The tip of claim 18, wherein the light adjusting module comprises a plate provided with a hole or a light reducing optical filter, and a lens for adjusting the focus size of the laser.

21. The tip of claim 18, wherein the light adjusting module is a convex lens which adjusts the focus size of the laser radiated toward the target, and the convex lens has a blocking layer for blocking a portion of the laser.

* * * * *